US007321007B2

(12) United States Patent
Gagliardi et al.

(10) Patent No.: US 7,321,007 B2
(45) Date of Patent: Jan. 22, 2008

(54) LIQUID ABSORBENT THERMOPLASTIC COMPOSITION COMPRISING SUPERABSORBENT MATERIAL PARTICLES OF SUBSTANTIALLY ANGLE-LACKING SHAPE

(75) Inventors: Ivano Gagliardi, Pescara (IT); Giovanni Carlucci, Chieti (IT); Roberto D'Addario, Pianella (IT); Paolo Veglio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 145 days.

(21) Appl. No.: 10/670,043

(22) Filed: Sep. 24, 2003

(65) Prior Publication Data
US 2004/0058159 A1 Mar. 25, 2004

(30) Foreign Application Priority Data
Sep. 24, 2002 (EP) .................................. 02021368

(51) Int. Cl.
*C08L 1/00* (2006.01)
*C08L 3/00* (2006.01)
*C08L 5/00* (2006.01)
*C08L 89/00* (2006.01)
*D21H 19/50* (2006.01)
*A61K 8/73* (2006.01)

(52) U.S. Cl. ........................... 524/13; 524/17; 524/21; 524/25; 524/27; 524/47; 524/55; 523/111

(58) Field of Classification Search ................. 524/17, 524/13, 21, 25, 27, 47, 55; 523/111
See application file for complete search history.

(56) References Cited
U.S. PATENT DOCUMENTS

| 4,952,618 | A | | 8/1990 | Olsen | |
| 4,977,211 | A | | 12/1990 | Doi | |
| 5,009,653 | A | | 4/1991 | Osborn, III | |
| 5,026,800 | A | * | 6/1991 | Kimura et al. | 526/200 |
| 5,378,472 | A | | 1/1995 | Muzzarelli | |
| 5,567,744 | A | | 10/1996 | Nagata | |
| 6,140,550 | A | * | 10/2000 | Beihoffer et al. | 604/366 |
| 6,465,379 | B1 | * | 10/2002 | Cook et al. | 442/393 |
| 6,562,742 | B2 | * | 5/2003 | Dutkiewicz et al. | 442/375 |
| 6,822,135 | B2 | * | 11/2004 | Soerens et al. | 604/366 |
| 6,849,672 | B2 | | 2/2005 | Mehawej et al. | |
| 2002/0039869 | A1 | | 4/2002 | Achille | |
| 2004/0065232 | A1 | | 4/2004 | Lykke | |

FOREIGN PATENT DOCUMENTS

| EP | 0 349 241 B1 | 8/1996 |
| EP | 1 013 291 A1 | 6/2000 |
| EP | 1 138 293 A1 | 10/2001 |
| EP | 1138293 * | 10/2001 |
| EP | 0 737 692 B1 | 1/2002 |
| EP | 1 193 289 A1 | 4/2002 |
| WO | WO 87/07618 A1 | 12/1987 |
| WO | WO 96/09023 A1 | 3/1996 |
| WO | WO 96/16624 A2 | 6/1996 |
| WO | WO 98/07618 A1 | 2/1998 |
| WO | WO 98/27559 A1 | 6/1998 |
| WO | WO 99/57201 A1 | 11/1999 |
| WO | WO 99/64505 A1 | 12/1999 |
| WO | WO 01/64153 A1 | 9/2001 |
| WO | WO 01/64154 A1 | 9/2001 |
| WO | WO 01/64155 A1 | 9/2001 |

OTHER PUBLICATIONS

PCT International Search Report dated Dec. 2, 2004.

* cited by examiner

*Primary Examiner*—Nathan M. Nutter
(74) *Attorney, Agent, or Firm*—Gary J. Foose; Kevin C. Johnson; David M. Weirich

(57) ABSTRACT

The present invention relates to a liquid absorbent thermoplastic composition, which contains particles of a superabsorbent material having angle-lacking shapes. The composition is particularly suitable to be used in absorbent articles for personal hygiene, specifically in disposable absorbent articles, which have one or more transparent regions.

3 Claims, 1 Drawing Sheet

LIQUID ABSORBENT THERMOPLASTIC COMPOSITION COMPRISING SUPERABSORBENT MATERIAL PARTICLES OF SUBSTANTIALLY ANGLE-LACKING SHAPE

FIELD OF INVENTION

The present invention relates to a liquid absorbent thermoplastic composition, which contains particles of a superabsorbent material having angle-lacking shapes. Said composition is particularly suitable to be used in absorbent articles for personal hygiene, specifically in disposable absorbent articles, which preferably comprise one or more regions in which they are transparent. In particular, the absorbent core of such transparent absorbent articles can be made from the liquid absorbent thermoplastic composition of the present invention.

BACKGROUND OF THE INVENTION

Absorbent articles for feminine hygiene, such as sanitary napkins and panty liners, are widely known in the art. The purpose of such articles is to absorb and retain body fluids, which are naturally excreted from the body. Such body fluids are any water based fluids or liquids excreted from the human body such as urine, menses, serum, blood, sweat, mucous as well as other aqueous solutions generally defined as body fluids. These articles typically comprise a liquid-pervious topsheet as wearer-facing layer, a liquid-impervious backsheet as garment-facing layer and an absorbent core between topsheet and backsheet. The body fluids are acquired through the topsheet and subsequently stored in the absorbent core. The backsheet prevents the absorbed fluids from wetting the wearer's garment.

It is also widely known in the art that it is beneficial for the absorption and retention characteristics of absoroent articles when portions of the article, typically the absorbent core, comprise superabsorbent materials, such as absorbent gelling material (AGM). An example for such articles is described in WO-A-01/64154.

Recent fashion trends have led to extensive use of cloths with a certain degree of translucency, which are especially worn by younger people, in particular women. Thus, as thereby the undergarment or even certain body portions can be noticed through such translucent cloths, a need exists for providing absorbent articles, which are not noticeable through the translucent cloths, as otherwise feelings of annoyance or irritation for the wearer of such articles or other people could arise.

Generally, absorbent articles are white or lightly pink coloured, but are always constructed of a material having a certain colour. As the backsheet is the part of the article with the highest potential of being noticed, adapting its colour in a way, which harmonizes with the colour of the undergarment, would be beneficial. However, as the colour of the undergarment is usually different from garment to garment, it would be impractical if the user had to purchase absorbent articles in different colours according to the actual undergarment.

Thus, it would be beneficial to provide absorbent articles of a colour, which does not contrast with any other colour. This condition is only fulfilled by substantially transparent, colourless articles. A substantially transparent absorbent article would require to be built exclusively from transparent components. Transparent topsheets and backsheets can be provided by using transparent polymeric films or thin pigment-free nonwovens. A problem to be solved is to provide an absorbent core, which is suitable to be used in substantially transparent absorbent articles. Traditionally, absorbent cores for use in disposable absorbent articles for feminine hygiene, such as sanitary napkins or panty liners, are made of a fibrous material, such as wood pulp, cotton or rayon. Typically, those cores comprise superabsorbent material for absorbing liquids and optional materials for e.g. controlling malodours. The drawback of such cores is the fact that all those materials are usually white coloured and could thus be easily noticeable through transparent topsheets and transparent backsheets.

To address this problem, absorbent cores, which substantially consist of a polymeric material containing superabsorbent material therein, have been suggested in the art. For instance, EP-A-1,138,293 discloses a substantially transparent absorbent article, comprising an absorbent core, which consists of a hot melt adhesive containing particles of an absorbent gelling material.

Adhesive materials having liquid absorbent properties are already known in the art. U.S. Pat. No. 4,952,618 discloses hydrocolloid/adhesive compositions, containing polycationic hydrocolloid particles, for use especially in wound dressings. Another water-absorbent composition is disclosed in U.S. Pat. No. 4,977,211. This document suggests the composition to be made from three components, which are a water-absorptive resin, a polyolefin resin and an ethylene/α-olefin copolymer. WO-A-98/27559 discloses a swellable hot melt adhesive for use in the production of watertight constructions, especially watertight cables. WO-A-99/57201 discloses a thermoplastic composition, which can be a hot melt adhesive, containing particles of a superabsorbent polymer for the prevention of gel blocking in absorbent articles. EP-A-1013291 discloses a hot melt adhesive containing fluid absorbing polymers for use in e.g. absorbent products, in particular for bonding substrates such as polymeric films together. WO-A-01/64153 and WO-A-01/64155 both disclose absorbent structures made by co-extruding a thermoplastic polymer with low melting point and a superabsorbent polymer for use as absorbent component in hygiene articles. WO-A-96/16624 discloses a stretchable absorbent core for stretchable absorbent articles. It is suggested in this document to build a core from superabsorbent particles, which are incorporated into a network of a stretchable binder, which is preferably a meltblown adhesive with elastic components. U.S. Pat. No. 5,567,744 discloses a high water-absorbent composition, which is obtained by fusing or fixing a thermoplastic resin onto a surface of a high water-absorbent resin via an adhesive binder or directly, for use in e.g. sanitary absorbent articles. WO-A-96/09023 discloses an adhesive coating containing superabsorbent particles for providing thinner absorbent structures for sanitary absorbent articles.

However, conventional absorbent compositions as described above typically suffer from a contradiction between sufficient liquid-absorbency for being used in absorbent articles and appropriate viscosity for being processed on conventional converter lines for producing such absorbent articles. This contradiction is caused by the fact that the higher the amount of superabsorbent material particles used in the compositions the higher is the viscosity of such compositions. Those prior art compositions have a viscosity at 150° C. of more than 20000 centipoises (cps) when their absorbency towards aqueous fluids is high enough, i.e. they contain a high amount of superabsorbent material particles, to make them suitable for absorbent articles. This viscosity is by far too high for processing such materials on conventional converter lines. Thus, for making such materials processable by reducing the viscosity to an acceptable value of about 15000 cps, the processing temperature has to be raised to more than 150° C. This again prevents the use of certain materials, such as polyethylene, as substrate materials, e.g. backsheets, for the application of the molten absorbent resin, because these materials would melt then themselves. On the other hand, when reducing the amount of superabsorbent material to reduce the viscosity of the composition, the liquid-absorbency of the resulting compositions is too low for being used in the field of absorbent articles in the context of the present invention.

Thus, there exists a need to provide an improved liquid absorbent thermoplastic composition, which has a good water-absorbency and which are easily processable by having for example a viscosity at 150° C. of not more than 15000 cps.

A further existing need is to provide an improved liquid absorbent thermoplastic composition, which has a good water-absorbency and which are easily processable by having for example a viscosity at 150° C. of not more than 15000 cps, and which has improved mechanical properties, such as high internal cohesion of the composition.

Furthermore, there exists a need for a composition of the aforementioned kind, which is substantially transparent, so that it can be used in substantially transparent absorbent articles.

It has now surprisingly been found that all the above needs can be satisfied by selecting particular superabsorbent particles, namely superabsorbent particles having a substantially angle-lacking, preferably approximately spherical shape, and an average particle diameter in dry state of between 0.1 µm and 500 µm. Superabsorbent particles having an angle-lacking shape are known from EP-A-349, 241, where a process for their production is suggested. However, there is no mentioning in the prior art towards the use of such particles in liquid-absorbent thermoplastic compositions, let alone in absorbent articles of personal hygiene.

SUMMARY OF THE INVENTION

The present invention relates to a liquid absorbent thermoplastic composition comprising a polymeric base material and particles of superabsorbent material, wherein said particles have a substantially angle-lacking shape and an average diameter of from 0.1 to 500 µm. The present invention relates also to the use of said composition in the absorbent core of disposable absorbent articles for personal hygiene, preferably transparent ones, and/or as loading indicator in such articles.

DETAILED DESCRIPTION OF THE INVENTION

Figure 1:
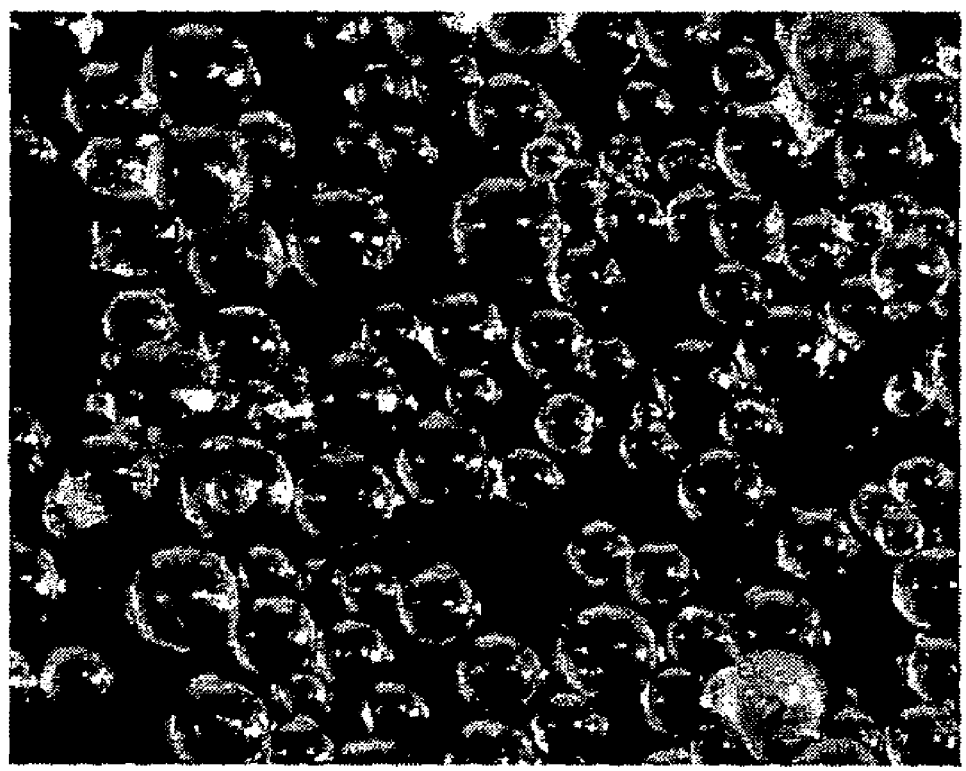
FIG. 1 shows a magnified view of approximately spherical particles of the superabsorbent material Aquakeep 10 SH-NF from Sumitomo Seika. The actual particle size of the particles showed in FIG. 1 is between 20 µm and 30 µm.

The term 'substantially transparent' as used herein refers to the ability of a material or combination of materials to transmit visible light through the body of the material. It is recognized that every material will remove a certain fraction of light and therefore complete transparency cannot exist. There are various possibilities to measure transparency, one of which is identified in the test methods section herein. The liquid absorbent thermoplastic composition of the present invention preferably has a transparency value of at least 50%, preferably at least 60%, more preferably at least 70%, even more preferably at least 80% and most preferably at least 90% according to the test method as disclosed herein ($\Delta E$ versus reference). Transparency has been measured with a homogeneous flat film of the liquid absorbent thermoplastic composition having a basis weight of 100 g/m$^2$ and a thickness of 100 µm.

The term 'absorbent article' is used herein in a very broad sense, including any article being able to receive and/or absorb and/or contain and/or retain body fluids. The absorbent article of the present invention typically comprises a fluid pervious topsheet as the layer contacting the skin of the wearer in use, a fluid impervious backsheet, which is preferably but not necessarily water vapour and/or gas pervious as the layer contacting the garment of the wearer in use, and an absorbent core, being positioned between the backsheet and the topsheet. All layers of the absorbent article (e.g. the topsheet, the backsheet and the absorbent core) have a wearer- and a garment-facing surface. When referring to absorbent articles, the requirement for transparency according to the present invention is that a colour be visually recognizable when viewed by the human eye through a region of the article, which is transparent through the thickness of said article. According to a preferred embodiment of the present invention, the article has at least one transparent region having a transparency value of at least 50%, preferably at least 60%, more preferably at least 70%, even more preferably at least 80% and most preferably at least 90% through the thickness of the article ($\Delta E$ versus reference). Particularly preferred absorbent articles in the context of the present invention are disposable absorbent articles. Preferred disposable absorbent articles according to the present invention are incontinence articles, perspiration pads, sanitary napkins or panty liners.

The term 'disposable' is used herein to describe absorbent articles, which are not intended to be laundered or otherwise restored or reused as an article (i.e. they are intended to be discarded after a single use and preferably to be recycled, composted or otherwise disposed of in an environmentally compatible manner).

The term 'use', as used herein, refers to the period of time that starts when the absorbent article is actually put in contact with the anatomy of the user.

By 'body fluid' it is meant herein any water based fluids or liquids excreted from the human body such as urine, menses, serum, blood, sweat, mucous as well as other aqueous solutions generally defined as body fluids, but it is not intended to exclude other water based fluids.

The term 'thermoplastic' as used herein refers to the ability of materials to soften and possibly even melt at raised temperatures and to harden again at reduced temperatures, while having substantially the same material characteristics after the hardening step as before the softening and/or melting step.

The liquid absorbent thermoplastic composition of the present invention comprises a polymeric base material and particles of superabsorbent material. Typically, the liquid absorbent thermoplastic composition of the present invention comprises from 5% to 99% by weight of the total composition of a polymeric base material and from 1% to 95% by weight of the total composition of particles of superabsorbent material.

The liquid absorbent thermoplastic composition of the present invention comprises as an essential element particles of superabsorbent material. Preferably, the liquid absorbent thermoplastic composition of the present invention comprises from 1% to 95%, preferably from 10% to 90%, more preferably from 30% to 70% and most preferably from 40% to 60% by weight of the total composition of particles of superabsorbent material. Any superabsorbent material known to the skilled person and used in absorbent articles, such as feminine care absorbent articles (e.g. sanitary napkins, panty liners or incontinence articles) or baby care absorbent articles (e.g. diapers) can be used herein. The particles of superabsorbent material for use herein are characterized by their substantially angle-lacking, preferably approximately spherical shape and their average particle size of from 0.1 µm to 500 µm.

Without the intention to be bound by any particular theory it is believed that the friction between angle-lacking particles is lower than the one between particles with angles, because mutual engagement or hooking together of the particles is much more likely in case of particles having a rougher surface, such as particles having shapes with angles. Because of this it is believed that the viscosity of a molten liquid absorbent thermoplastic composition having particles therein with angle-lacking shape is significantly lower than the viscosity of a molten liquid absorbent thermoplastic composition with particles having shapes with angles at the same temperature, such as those disclosed by the prior art described infra. The liquid absorbent thermoplastic composition of the present invention typically has a viscosity at about 150° C. of not more than 15000 centipoises, preferably not more than 12000 centipoises, more preferably not more than 10000 centipoises, even more preferably not more than 8000 centipoises and most preferably not more than 5000 centipoises. The viscosity values discussed herein have been determined by the viscosity test method as disclosed herein. It is also believed that particles with substantially angle-lacking shape have a higher transparency due to their smoother surface compared to particles with a rougher surface due to shapes with angles, like the ones being used in the prior art as described infra.

'Particles' as used herein refers to discrete flakes, fibres, beads and the like or mixtures thereof, of a certain material, in particular superabsorbent material. The term particles herein also comprises agglomerations or aggregations of discrete flakes, fibres, beads and the like of a certain material. 'Particle size' as used herein means the weighted average of the smallest dimension of the individual particles.

'Angle lacking' as used herein refers to the shape of particles, which can be of spherical or non-spherical shape and which have no sharp angles in their shapes and on their surfaces. According to the present invention the shape of an amount of particles is considered as angle lacking, if at least 70%, preferably at least 80% more preferably at least 90%, even more preferably at least 95% and most preferably 100% of the regarded amount of particles have an angle lacking shape according to the definition hereinbefore.

'Spherical' as used herein refers to particles having an angle-lacking shape, which have a substantially roundish or ball-like shape. A spherical particle according to the present invention is characterized in that the ratio of its largest dimension divided by its smallest dimension is not larger than 1.5 and is preferably 1.

The average particle size of the particles of superabsorbent material for use herein is in dry state from 0.1 µm to 500 µm, preferably from 1 µm to 200 µm, more preferably from 10 µm to 100 µm, even more preferably from 10 µm to 60 µm and most preferably from 15 µm to 40 µm. Without the intention to be bound by theory it is believed that the smaller the average diameter of the particles of superabsorbent material are, the better their absorbency towards liquids is. Indeed the effective surface area, which is in contact with the liquid to be absorbed, is much larger for a large quantity of small particles compared to a smaller quantity of larger particles of the same overall weight. A particle size of the superabsorbent particles of smaller than 0.1 µm results in process problems, as by the very fine particles the generation of dust while handling those particles, e.g. during manufacture of the composition of the present invention, is highly likely. On the other hand, when using superabsorbent particles being larger in diameter than 500 µm, it is not possible anymore to provide thin layers of the composition of the present invention. The minimum thickness of such a layer is determined by the diameter of the superabsorbent particles.

'Superabsorbent material' as used herein means materials, which are capable of absorbing at least five times of their weight of water or aqueous liquids. Preferred superabsorbent materials are anionic absorbent gelling material as well as cationic absorbent material, such as chitin, chitosan or chitosan compounds, or combinations of anionic and cationic superabsorbent material. Particularly preferred superabsorbent materials for use herein are anionic absorbent gelling materials, i.e., absorbent gelling materials, which are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Generally, the functional groups are attached to a slightly cross-linked acrylic base polymer. Superabsorbent materials for use according to the present invention can be made by polymerisation of ethylenically unsaturated monomers. Examples of ethylenically unsaturated monomers are acrylic acid, methacrylic acid, crotonic acid, maleic acid and its anhydride, fumaric acid, itaconic acid, and 2-(meth)acryloylethanesulfonic acid, and 2-(meth) acryloylpropanesulfonic acid, and 2-(meth)acrylamido-2-methylpropanesulfonic acid, vinylsulfonic acid, styrenesulfonic acid and the like and their salts; monomers containing nonionic hydrophilic substituents such as (meth) acrylamide, N-substituted (meth)acrylamides, 2-hydroxyethyl (meth)acrylate, 2-hydroxypropyl (meth)acrylate, methoxypolyethylene glycol (meth)acrylate, polyethylene glycol (meth)acrylate and the like; monomers of cationic character such as N,N'-dimethylaminoethyl (meth)acrylate, N,N'-diethylaminoethyl (meth)acrylate, N,N',N,N'-diethylaminopropyl (meth)acrylate, N,N'-dimethylaminopropyl (meth)acrylamide, and the like and their quartary salts. The polymers of those monomers can be used alone or mixtures of the polymers two or more of those monomers can be used as well. Copolymers of these monomers can also be used. Especially preferred polymers for use as superabsorbent material are cross-linked polyacrylates, hydrolyzed acrylonitrile grafted starch, polyacrylates grafted starch and isobutylene maleic anhydride copolymers.

Suitable crosslinking agents for facilitating the crosslinking of the preferred absorbent gelling material for use as superabsorbent material are N,N'-methylene-bis(meth)acrylamide, N-methylol(meth)acrylamide, ethylene glycol (meth)acrylate, polyethylene glycol (meth)acrylate, propylene glycol (meth)acrylate, polypropylene glycol (meth) acrylate, glycerol tri(meth)acrylate, glycerol mono(meth)

acrylate, polyfunctional metal salts of (meth)acrylic acid, trimethylolpropane tri(meth)acrylate, triallylamine, triallyl cyanulate, triallyl isocyanulate, triallyl phosphate, glycidyl (meth)acrylate. As examples of agents having reactive functional groups for example, in a case that a monomer has a carboxyl and/or carboxylate group, polyhydric alcohol derivatives such as ethylene glycol, diethylene glycol, triethylene glycol, tetraethylene glycol, polyethylene glycol, glycerol, polyglycerol, propylene glycol, diethanolamine, triethanolamine, polyoxypropylene, oxyethyleneoxypropylene block co-polymer, pentaerythritol, and sorbitol; polyglycidyl derivatives such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and polypropylene glycol diglycidyl ether; aziridine derivatives and related compounds such as 2,2-bishydroxymethylbutanol-tris (3-[1-aziridinyl) propionate], 1,6-hexamethylenediethylene urea, and diphenylmethane-bis-4,4'-N,N'-diethylene urea; haloepoxyl compounds such as epichlorohydrin and alpha-methylchlorohydrin; polyaldehydes such as glutar aldehyde and glyoxal; poly amine derivatives such as ethylene diamine, diethylene triamine, triethylene tetramine, tetraethylene pentamine, pentaethylene hexamine, and polyethylene hexamine; polyisocyanates such as 2,4-toluylenediisocyanate and hexamethylenediisocyanate; polyvalent metal salts such as aluminium chloride, magnesium chloride, calcium chloride, aluminium sulfate, magnesium sulfate, and calcium sulfate. Subject to consideration upon reactivity, these crosslinking agents can be used as a mixture of more than two, but it is usually preferable to use a crosslinking agent having polymerizable unsaturated groups.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

Examples for cationic superabsorbent materials for use herein are chitin, chitosan, chitosan salts, such as chitosonium lactate or chitosonium pyrollidone carboxylate (as disclosed in WO-A-98/07618), modified chitosans as disclosed in WO-A-87/07618, U.S. Pat. No. 5,378,472 or EP-A-737,692, cross-linked chitosans, or mixtures thereof FIG. 1 shows approximately spherical particles of a superabsorbent material suitable for use herein, namely particles of Aquakeep 10 SH-NF, available from Sumitomo-Seika, having a particle size of between 20 µm and 30 µm. Another example for substantially angle-lacking particles of superabsorbent material suitable for use herein is Aquakeep 10 SH-P, also from Sumitomo-Seika. The latter material is often referred to as 'broccoli-like', as the individual particles of this material are basically an agglomeration of substantially spherical particles of superabsorbent material.

The liquid absorbent thermoplastic composition of the present invention comprises as a further essential element a polymeric base material. Typically, the liquid absorbent thermoplastic composition of the present invention comprises from 5% to 99%, preferably 10% to 90%, more preferably from 30% to 70%, most preferably from 40% to 60% by weight of the total composition of a polymeric base material. Any polymeric base material known to the skilled person and used in the construction of absorbent articles, such as feminine care absorbent articles (e.g. sanitary napkins, panty liners or incontinence articles) or baby care absorbent articles (e.g. diapers) can be used herein.

The polymeric base materials for use herein comprise from 5% to 99%, preferably 10% to 90%, more preferably from 30% to 70%, most preferably from 40% to 60% per weight of thermoplastic polymers as an essential element. A variety of different thermoplastic polymers are suitable for use herein. Exemplary thermoplastic polymers for use with the present invention are block copolymers, amorphous and crystalline polyolefins including homogeneous and substantially linear ethylene/alpha-olefin interpolymers, interpolymers of ethylene such as ethylene-vinyl-acetate (EVA), ethylene-methyl-acrylate (EMA) and ethylene n-butyl acrylate (EnBa) and mixtures thereof.

A wide variety of 'block copolymers' are useful in the present invention. The group of block copolymers includes linear copolymers of the triblock A-B-A or the diblock A-B type, or radial co-polymer structures having the formula $(A-B)_x$. The A blocks are non-elastic polymer blocks, typically polyvinylarene blocks, the B blocks are unsaturated conjugated dienes, such as poly(monoalkenyl) blocks, or hydrogenated versions thereof, x denotes the number of polymeric arms, and x is an integer greater than or equal to one. Suitable block A polyvinylarenes include, but are not limited to polystyrene, polyalpha-methylstyrene, polyvinyltoluene, and combinations thereof. Suitable block B poly (monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Europrene™ Sol T from EniChem, Kraton™ elastomers from Shell Chemical Company, Vectorm elastomers from Dexco, Solprene™ from Enichem Elastomers and Stereon™ from Firestone Tire & Rubber Co.

Amorphous polyolefins or amorphous polyalphaolefins (APAO) are homopolymers, copolymers, and terpolymers of $C_2$-$C_8$ alphaolefins. These materials are typically polymerised by means of processes, which employ Ziegler-Natta catalysts resulting in a relatively broad molecular weight distribution. Commercially available amorphous polyalphaolefins include Rextac™ and REXFlex™ propylene based homopolymers, ethylene-propylene copolymers and butene-propylene copolymers available from Rexene (Dallas, Tex.) as well as Vestoplast alpha-olefin copolymers available from Huls (Piscataway, N.J.).

Metallocene polyolefins are homogeneous linear and substantially linear ethylene polymers prepared using single-site or metallocene catalysts. Homogeneous ethylene polymers are characterized as having a narrow molecular weight distribution and a uniform short-chain branching distribution. In the case of substantially linear ethylene polymers, such homogeneous ethylene polymers are further characterized as having long chain branching. Substantially linear ethylene polymers are commercially available from The Dow Chemical Company as Affinity™ polyolefin plastomers, which are produced using Dow's Insite™ technology, whereas homogeneous linear ethylene polymers are available from Exxon Chemical Company under the tradename Exactm. Homogeneous linear and substantially linear ethylene polymers having a relatively low density, ranging from about 0.855 to about 0.885, and a relatively low melt index, for example less than about 50 g/10 min are most preferred, particularly for creating elastomeric fibers, films and adhesive compositions that swell upon exposure to water.

The term 'interpolymer' is used herein to indicate a copolymer, terpolymer, or higher order polymer. That is, at least one other comonomer is polymerized with ethylene to make the interpolymer. Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof.

If employed uncompounded, the ethylene to unsaturated carboxylic comonomer weight ratio is preferably greater than about 3:1, more preferably about 2:1. Hence, the comonomer concentration is preferably greater than 30 wt-%, more preferably greater than 33 wt-% and most preferably greater than 35 wt-%, with respect to the total weight of the ethylene interpolymer. The melt index of the interpolymers of ethylene may range from about 50 to about 2000, preferably from about 100 to 1500, more preferably from about 200 to 1200, and most preferably from about 400 to 1200 g/10 min. When employing a polymer having too low of a melt index uncompounded, the strength of the polymer tends to constrain the swelling of the particles of superabsorbent material.

Suitable ethylene/unsaturated carboxylic acid, salt and ester interpolymers include ethylene/vinyl acetate (EVA) ethylene/acrylic acid (EEA) and its ionomers; ethylene/methacrylic acid and its ionomers; ethylene/methyl acrylate (EMA); ethylene/ethyl acrylate; ethylene/n-butyl acrylate (EnBA); as well as various derivatives thereof that incorporate two or more comonomers.

Other suitable thermoplastic polymers that may be employed include polylactide, caprolactone polymers, and poly (hydroxy-butyrate/hydroxyvalerate), certain polyvinyl alcohols, biodegradable copolyesters such as Eastman Copolyester 14766 (Eastman), linear saturated polyesters such as Dynapol or Dynacoll polymers from Huls, poly (ethylene oxide) polyether amide and polyester ether block copolymers available from Atochem (Pebax™, e.g. Pebax MV 3000) or Hoechst Celanese (Rite-flex™) respectively, and polyamide polymers such as those available from Union Camp (Unirez™) or Huls (Vestamelt™) or EMS-Chemie (Griltex™). Other suitable thermoplastic polymers are e.g. polyurethanes, poly-ether-amides block copolymers, polyethylene-acrylic acid and polyethylene-methacrylic acid copolymers, polyethylene oxide and its copolymers, ethylene acrylic esters and ethylene methacrylic esters copolymers, polylactide and copolymers, polyamides, polyesters and copolyesters, polyester block copolymers, sulfonated polyesters, poly-ether-ester block copolymers, poly-ether-ester-amide block copolymers, ionomers, polyethylene-vinyl acetate with a vinyl acetate content of at least 28% by weight, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, poly-caprolactone and copolymers, poly glycolide, polyglycolic acid and copolymers, polylactic acid and copolymers, polyureas, polyethylene, polypropylene, or mixtures thereof.

Particularly suitable preferred thermoplastic polymers are selected from thermoplastic poly-ether-amide block copolymers (e.g. Pebax™), thermoplastic poly-ether-ester-amide block copolymers, thermoplastic polyester block copolymers (e.g. Hytrel™, e.g. Hytrel 8171), thermoplastic polyurethanes (e.g. Estane™), or mixtures thereof.

The polymeric base materials for use herein preferably furthermore comprise from 5% to 90%, preferably 10% to 85%, more preferably from 15% to 70%, most preferably from 30% to 65% by weight of suitable compatible plasticizers. Suitable 'plasticizers' for use in the present invention generally will include any conventional plasticizers which decrease hardness and modulus, enhance pressure sensitive tack and reduce melt and solution viscosity. It is preferred that the plasticizer be water soluble or water dispersible or alternatively be a wax-like substance such as polyethylene or polypropylene glycol, glycerin, glycerol and its esters, butylene glycol or sorbitol. Other plasticizers suitable for use in the present invention are esters of sucrose; phthalate plasticizers such as dioctyl phthalate and butyl benzyl phthalate (e.g., Santicizer 160 from Monsanto); benzoate plasticizers such as 1,4-cyclohexane dimethanol dibenzoate (e.g., Benzoflex 352 from Velsicol), diethylene glycol/dipropylene glycol dibenzoate (e.g., Benzoflex 50 from Velsicol), and diethylene glycol dibenzoate where the mole fraction of hydroxyl groups which have been esterified ranges from 0.5 to 0.95 (e.g., Benzoflex 245 High Hydroxyl also from Velsicol); phosphite plasticizers such as t-butyl diphenyl phosphate (e.g., Santicizer 154 from Monsanto); adipates; sebacates; epoxidized vegetal oils; polymerised vegetal oils; polyols; phthalates; liquid polyesters such as Dynacol 720 from Huls; glycolates; p-toluene sulfonamide and derivatives; glycols and polyglycols and their derivatives; sorbitan esters; phosphates; monocarboxylic fatty acids ($C_8$-$C_{22}$) and their derivatives; liquid rosin derivatives having Ring and Ball hydrocarbon oils which are low in aromatic content and which are paraffinic or naphthenic in character and mixtures thereof. Plasticizer oils are preferably low in volatility, transparent and have as little color and odor as possible. An example of a preferred plastizer is Carbowax™ polyethylene glycol from Union Carbide. Other preferred plasticizers are PEG 400 and PEG 1500 from Aldrich. The use of plasticizers in this invention also contemplates the use of olefin oligomers, low molecular weight polymers, vegetable oils and their derivatives and similar plasticizing liquids.

According to a preferred embodiment of the present invention particularly preferred plasticizers to be used herein are hydrophilic plasticizers such as acids, esters, amides, alcohols, polyalcohols, or mixtures thereof, among which even more preferred are citric acid esters, tartaric acid esters, glycerol and its esters, sorbitol, glycolates, and mixtures thereof, as disclosed in our application WO 99/64505. Said preferred hydrophilic plasticizers have a particularly high polar character and provide the further advantage that they do not impair, and possibly can even enhance, the moisture vapour permeability of the resulting layer or film formed from the polymeric base material and thus the liquid absorbent thermoplastic composition of the present invention comprising said preferred plasticizer or blend of plasticizers, when compared to a corresponding film or layer formed from an liquid absorbent thermoplastic composition comprising the same components, but without the plasticizer or plasticizers.

These particularly preferred hydrophilic plasticizers or blends of hydrophilic plasticizers can of course also adjust the viscosity of the polymeric base material and thus the liquid absorbent thermoplastic composition according to the present invention. Thus, the viscosity can be fine-tuned to the preferred values disclosed infra in order to make said composition processable.

Plasticizers selected among those described in European patent application EP 1,193,289 can also be used herein. Said plasticizers can be selected from the group consisting of esters of phosphoric acid; esters of benzoic, phthalic and trimellitic acids; esters of polycarboxylic oxy-acids; sulphonamides and their derivatives such as sulphonamide-form-aldehyde resins; sulfones; esters of poly-valent alcohols; lactides; glycolides; lactones; lactams. Said plasticizers are capable of also providing the polymeric base material and thus the liquid absorbent thermoplastic composition with a certain degree of tackiness.

The polymeric base material for use in the liquid absorbent thermoplastic composition of the present invention optionally also comprises from 0% to 100%, preferably 1% to 30%, more preferably from 5% to 20%, most preferably from 8% to 12% by weight of tackifying resins. As used herein, the term 'tackifying resin' means any of the liquid absorbent thermoplastic compositions described below that are useful to impart tack to the polymeric base material. ASTM D1878-61T defines tack as "the property of a material which enables it to form a bond of measurable strength immediately on contact with another surface". Tackifying resins comprise resins derived from renewable resources such as rosin derivatives including wood rosin, tall oil and gum rosin as well as rosin esters, natural and synthetic terpenes and derivatives of such. Aliphatic, aromatic or mixed aliphaticaromatic petroleum based tackifiers are also useful in the invention. Representative examples of useful hydrocarbon resins include alpha-methyl styrene resins, branched and unbranched $C_5$ resins, $C_9$ resins and $C_{10}$ resins, as well as styrenic and hydrogenated modifications of such. Tackifying resins range from being a liquid at 37° C. to having a ring and ball softening point of about 135° C. Suitable tackifying resins for use herein include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof; aromatic petroleum resin and the hydrogenated derivatives thereof; and aliphatic or aromatic petroleum resins and the hydrogenated derivatives thereof, and combinations thereof. Commercial examples of these types of resins include Foral™ hydrogenated rosin ester, Staybelite™ hydrogenated modified rosin, Polypale™ polymerized rosin, Permalyn™ rosin ester, Pentalyn™ rosin ester, Adtac™ oil extended hydrocarbon resin, Piccopale™ aromatic hydrocarbon, Piccotac™, Hercotac™ aromatic modified aliphatic hydrocarbon, Regalrez™ cycloaliphatic resins, or Piccolyte™ from Hercules, Eselementz™ from Exxon Chemical aliphatic hydrocarbon and cycloaliphatic resins, Wingtack™ from Goodyear Tire & Rubber Co. synthetic polyterpene resins including aromatic modified versions, Arkon™ partially and fully hydrogenated aromatic resins from Arakawa Chemicals, Zonatac™ styrenated terpene resin, Zonarez™ rosin ester and Zonester™ rosin ester from Arizona Chemical and Nevtac™ aromatic modified aliphatic hydrocarbon from Neville Chemical Company.

The polymeric base material for use in the liquid absorbent thermoplastic composition of the present invention optionally also comprises from 0.1% to 10%, preferably 0.2% to 5%, more preferably from 0.5% to 2%, most preferably from 0.75% to 1.5% by weight of anti-oxidants. Suitable 'anti-oxidants' for use in the present invention include any conventional anti-oxidants, and are preferably hindered phenols such as for example Ethanox 330™ 1,3,5-trimethyl-2,4,6-tris(3,5-di-tert-butyl-4-hydroxybenzyl) benzene which is commercially available from the Ethyl Corporation. Other examples for suitable anti-oxidants are hindered phenolics (e.g., Irganox 1010, Irganox 1076, Irganox B 225).

The polymeric base material for use in the liquid absorbent thermoplastic composition of the present invention optionally also comprises surfactants. Suitable 'surfactants' for use herein are additives that reduce the surface tension and/or contact angle of the polymeric base material. Surfactants are useful in amounts ranging from about 0% to about 25% by weight and preferably from about 5% to about 15% by weight, with respect to the total weight of the polymeric base material. Suitable surfactants include nonionic, anionic, and silicone surfactants. Exemplary nonionic surfactants are: Ethoxylates of (i) $C_1$-$C_{18}$, preferred $C_8$-$C_9$ alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl $C_8$-$C_{60}$ monoalcohols, such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having a Mn of 200 to 3000, available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred nonionic surfactant blend is Atmer 685, available from ICI Surfactants (Wilmington, Del.). Suitable anionic surfactants are: $C_8$-$C_{60}$ alkyl ethoxylate sulfonates, $(CH_3-(CH_2)_{11-14}-(O-CH_2-CH_2)_3-SO_3^-Na^+$, such as, Avenel S30, available from PPG Industries; alkyl $C_8$-$C_{60}$ sulfonates like sodium dodecyl sulfate (SDS), such as Rhodapon UB ($C_{12}-SO_3^-Na^+$) available from Rhone Poulenc; and alkyl/aromatic sulfonates, such as those sold under the tradename Calsoft. Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 available from OSi Specialties, Danbury, Conn.; and product 193 from Dow Corning. The preferred surfactants are those with lower molecular weights because these have increased compatibility in the polymeric base material. The maximum acceptable molecular weight depends on the type of surfactant and the other ingredients in the polymeric base material and thus the liquid absorbent thermoplastic composition of the present invention.

Other optional components of the polymeric base material for use herein include anti-ultraviolets, dyes (as long as they do not compromise the transparency of the composition), antibacterials, odour adsorbing materials, perfumes, pharmaceuticals, and mixtures thereof, which may be present within the liquid absorbent thermoplastic compositions at a level of up to 10% by weight of the composition.

The liquid absorbent thermoplastic composition of the present invention is preferably a hot-melt adhesive, i.e. the polymeric base material comprises a hot-melt adhesive, which is capable of absorbing aqueous liquids. Such preferred liquid absorbent thermoplastic compositions comprise (by weight):

a) from about 5% to about 99% of a polymeric base material, comprising
   a') from about 10% to about 50% of a block copolymer,
   a") from about 0% to about 50% of a tackifying resin; and
b) from about 1% to about 95% of particles of superabsorbent material having substantially angle-lacking shapes and having an average particle diameter in dry state of from 0.1 μm to 500 μm.

As the preferred liquid absorbent thermoplastic composition of the present invention is substantially transparent, it is beneficial that all its components are substantially transparent as well. However, it is also possible that components, which are not substantially transparent, can result in a substantially transparent liquid absorbent thermoplastic composition once mixed, e.g. by interaction, such as chemical reaction, with other components of the absorbent composition.

Another preferred embodiment of the preferred substantially transparent liquid absorbent thermoplastic composition of the present invention is the following hot-melt adhesive composition, comprising (by weight):

a) from about 5% to about 99% of a polymeric base material, comprising
   a') from about 10% to about 50% block copolymer,
   a'') from about 0% to about 50% tackifying resin,
   a''') from about 10% to about 80% plasticizer,
   a'''') from about 0% to about 2% antioxidant; and
b) from about 1% to about 95% of particles of superabsorbent material having substantially angle-lacking shapes and having a an average particle diameter in dry state of from 0.1 µm to 500 µm.

Highly preferred thermoplastic polymeric base materials for use in the liquid absorbent thermoplastic compositions described herein before are those having a water absorption capacity of at least 30%, preferably more than 40%, more preferably more than 60% and most preferably more than 90%, when measured according to the Water Absorption Test described herein in accordance with ASTM D 570-81, on a 200 µm thick film. The intrinsic absorbency of the polymeric base material/matrix allows for a more effective diffusion of the body fluid within the matrix and, consequently, for a better spreading of the body fluid, which can reach a greater number of absorbent material particles, which in turn give rise to a better utilization of the absorbent material.

Highly preferred liquid absorbent thermoplastic compositions described herein before are those having improved mechanical properties, such as good integrity in wet state thanks to good internal cohesion and hence having a tensile strength in wet state which is at least 20%, preferably at least 40%, and more preferably at least 60% of the tensile strength of said composition in dry state. Said tensile strengths are evaluated according to the Tensile Strength Test described herein. It should be appreciated that by selecting a thermoplastic base material in the liquid absorbent thermoplastic composition herein having a higher value of water absorption, the absorbent composition will have better liquid absorption/handling characteristics, while not compromising on tensile strength in wet state. Indeed such absorbent composition will remain substantially intact and have sufficient tensile strength for its intended use, also upon liquid absorption.

Indeed the highly preferred liquid absorbent thermoplastic compositions for use herein offer improved mechanical and absorbent properties. Without to be bound by theory it is believed that the intrinsic absorbency of the matrix allows the body fluid to be acquired and diffused within the matrix thus permitting fluid contact with the absorbent material contained in the matrix and their swelling, without the necessity of having a matrix of low cohesive strength but with a matrix, which remains substantially intact and having sufficient strength upon fluid absorption.

The absorbent in particle form is blended with the polymeric base material in any known manner to provide the liquid absorbent thermoplastic composition for use herein. For example, by first melting the thermoplastic polymeric base material and then by adding and mixing the required amount of absorbent material particles. Suitable adhesive processing equipments can be used such as a melt mixer or extruder. Preferably the liquid absorbing thermoplastic compositions for use herein are formulated to have hot melt adhesive characteristics so that they can be applied utilizing any known method used for applying hot melt adhesives.

At least at the coating temperature, since the liquid absorbent thermoplastic composition comprises thermoplastic polymeric base materials, it can exhibit adhesive properties on a supportive substrate in order to form a composite structure such that no additional adhesive is required to achieve a permanent attachment between the absorbent element, which is provided partially or preferably completely by the liquid absorbent thermoplastic composition, and the substrate. However, while hot melt techniques are preferred, any other known method for processing thermoplastic compositions can be used for processing the absorbent compositions in any known form/pattern. Also, any known method for spraying, printing, dotting, coating or foaming thermoplastic compositions can be used as well as extrusion or lamination processes.

Particularly suitable methods for applying the liquid absorbent thermoplastic composition to a substrate are gravure printing or slot coating. Both methods are particularly suitable for discontinuous application of the thermoplastic composition described herein onto a substrate. The gravure print unit or slot coater applies the thermoplastic composition in the desired pattern onto a substrate.

In its broadest embodiment the present invention also encompasses the use of a substantially transparent liquid absorbent thermoplastic composition containing particles of superabsorbent material having a substantially angle-lacking shape, as a loading indicator e.g. in disposable absorbent articles. Therefore, one layer of the article has to comprise the composition of the present invention in a visually noticeable manner, preferably as a film. A possible embodiment could be provided in that the composition of the present invention is provided underlying the topsheet of an absorbent article, preferably as a film, so that said composition is visible to the user through the topsheet. The topsheet can be either transparent or can alternatively have apertures through which said film is visible. The fuctionality of such a loading indicator is as follows: Due to the swelling of the particles of superabsorbent material, when subjected to aqueous fluids, there is a visually-noticeable difference in the diffraction and/or absorption of light trespassing through the composition of the present invention between its wet and its dry state, in particular the composition is becoming more opaque when wet. This visually recognizable increase in opaqueness of the composition of the present invention when wetted can be used as a loading indicator for the wearer of such an article.

In a preferred embodiment the liquid absorbent thermoplastic composition is substantially transparent. The preferred substantially transparent liquid absorbent thermoplastic composition of the present invention is suggested to be used in the field of absorbent articles, preferably transparent absorbent articles. In particular it is suggested to use the substantially transparent liquid absorbent thermoplastic composition for the construction of the absorbent core of substantially transparent absorbent articles. Such substantially transparent absorbent articles have at least one region, which is transparent through its thickness. Preferably, the entire absorbent article is transparent through its thickness. In a preferred embodiment, a transparent absorbent article has a transparent topsheet, a transparent backsheet and a transparent absorbent core comprising the liquid absorbent thermoplastic composition of the present invention.

Suitable topsheets are compliant, flexible, soft feeling and non-irritating to the wearer's skin. The topsheet can be made from a nonwoven or woven material or a film that has been rendered liquid-pervious by aperturing.

In general the backsheet is compliant, flexible and soft feeling. The backsheet prevents the body fluids absorbed and contained in the absorbent core from wetting clothes that contact the absorbing article, such as undergarments. Preferably the backsheet is impervious to liquids (e.g., menses, sweat and/or urine). It can be manufactured from a thin plastic film, although other flexible liquid impervious materials can also be used. As used herein, the term "flexible" refers to materials that are compliant and will readily conform to the general shape and contours of the human body. The backsheet preferably also can have elastic characteristics allowing it to stretch in one or two directions. Furthermore it is preferred that the backsheet for use herein is breathable, i.e. being pervious to gases/vapour while being impervious to liquids.

The topsheet and the backsheet can be completely transparent or can be provided only with regions of transparency. Suitable materials for the topsheet or backsheet for use herein can be found g.e. in EP-A-1,138,293. An example for suitable topsheet materials is an apertured polyethylene formed film, e.g. transparent CPM DH TM available from BP Chemicals. An example for suitable backsheet materials is a nonwoven without pigment, e.g. code W16Fio, basis weight 16 g/m$^2$, available from BBA Corovin.

The liquid absorbent thermoplastic composition of the present invention can be used in absorbent articles, preferably in substantially transparent ones, as the absorbent core. In a preferred embodiment, the liquid absorbent thermoplastic composition is used as the sole material comprising the core, being directly adjacent to a substantially transparent topsheet and a substantially transparent backsheet. Alternatively, the liquid absorbent thermoplastic composition can comprise optional components as part of the absorbent core. Such optional components are fluid distribution layers, optional fibrous layers, reinforcing scrims or odour control materials for counteracting malodours. If present, these materials are chosen to be transparent as well. Suitable materials for those optional components are disclosed in EP-A-1,138,293.

Absorbent articles according to a preferred embodiment of the present invention are constructed like conventional articles with the exception that the conventional means for joining portions of material together must be carefully considered to ensure that the objective of creating a transparent region is not lost. For instance the adhesive used to join the topsheet to the backsheet in the region outside the absorbent core should either be transparent or it should be eliminated and be replaced by e.g. crimping.

The transparency as indicated above can be used beneficially in the context of sanitary napkins, panty liners and sweat pads (underarm or collar). A new product design, which is a sub-form of a sanitary napkin or panty liner form, namely thong shaped sanitary napkins or panty liners, so called thong liners, are particularly susceptible to the present invention. The thong liner design is such that it provides the sanitary napkin or panty liner with a shape such that it can be worn in thong slips, G-string undergarments or string panties, hence the thong shape is fundamentally triangular or trapezoidal.

In general, all typically used components in absorbent products can also be comprised in the preferred absorbent articles according to the present invention as long as the absorbent article comprises at least one region of transparency.

Most preferred, the absorbent articles will comprise a fastening adhesive for attachment. The design of the fastening adhesive must be selected such that it does not interfere with the desired transparency, but transparent adhesives will ensure that. In the case of sanitary napkins, panty liners or thong liners, a so called panty fastening adhesive is preferred to be present on the backsheet for attachment to an undergarment. However, for sweat pads, e.g. underarm sweat pads, either attachment to an adjacent garment or attachment to the skin of the wearer directly can also be considered. Of course, such direct skin attachment, which is conventionally provided by water gel, hydrogel or oil gel based body adhesives can also be used in sanitary napkins or body liners (in contrast to panty liners).

Test Procedures:

a) Transparency Test

General Definition

'Optically transparent' as used herein means permitting the passage of light radiation. 'Optically transparent medium' as used herein means a medium, which has the property of transmitting rays of lights in such a way that the human eye may see through the medium distinctly.

In general, transparency is the ability of a material to transmit light through itself and, consequently, by the transparency it is possible to see e.g. objects or colours or printed or written text through such material.

According to the above terminology transparency of a product is defined by:
1. having the property of transmitting rays of light in such a way that written or printed text/characters and colours located opposite the transparent product can be clearly viewed by the human eye.

and/or 2. having the property of transmitting rays of light in such a way that the human eye may see through the product.

One of the main advantages delivered by a transparent product is that its presence (colour) is less recognizable by the human eye, such that, in case of absorbent articles for feminine hygiene, the colour of the undergarment (or other clothing) is recognizable (visual discreteness, no product awareness).

Colours can be measured according to the CIELAB colour system (CIE 1976 L*a*b*). The CIELAB colour space can be visualized as a three dimensional space, where every colour can be uniquely located. The location of any colour in the space is determined by its colour coordinates; L*, a*, b*. In other words, all colours that are perceived by the human eye are converted into a numerical code.

When a colour is defined according to this system L* represents lightness (0=black, 100=white), a* and b* independently each represent a two colour axis, a* representing the axis red/green (+a=red, −a=green), while b* represents the axis yellow/blue (+b=yellow, −b=blue).

ΔE represents graphically the distance between two colours. In this case, ΔE represents the distance between the reference colour and the centre of the sphere of the 3d model (L*=50, a*=0, b*=0).

$$\Delta E = [(\Delta L)^2 + (\Delta a)^2 + (\Delta b)^2]^{1/2}$$

The ability to see a colour through a material (or product) is measured as an index of transparency. If a material is 100% transparent, it is possible to measure the same L*, a*, b* and ΔE value for the above colour alone and through the material. As a reference the colour white is used. The closer the colour is to the white reference (when both are viewed through the material/product) the less transparent that material (or product) will be considered.

Colour Transparency Methodology

Colour can measured using the colorimeter MINOLTA model CR-300 instrument (available from the Minolta Company, Japan) which provides the coordinates L*, a*, b* and from which the ΔE value can be determined.

The standard colours used in this measurement are the primary colours Cyan, Magenta and Yellow references of PANTONE Colour Specifier 747XR and the white calibration reference plate of the colorimeter instrument.

The colour grade coordinate values for the material to be tested for each of the colour references Cyan, Magenta and Yellow is determined by placing the material or product on the colour specific reference and taking a reading from the colorimeter and calculating ΔE.

For each of the reference colours (rc) the ΔE value is recalculated by setting the scale such that $\Delta E_{rc}$ result, referred to as $\Delta\Delta E_{rc}$ is zero (i.e. 100% transparent) and that $\Delta E_{white}$ with respect to the reference colour is referred to as $\Delta\Delta_w$, which is 62.2 for example and represents 0% transparency.

This can be represented by the formulae below:

$$\Delta\Delta E_{rc}=[(L_{rc}-L_{rc})^2+(a_{rc}-a_{rc})^2+(b_{rc}-b_{rc})^2]^{1/2}=0$$

$$\Delta\Delta E_w=[(L_{rc}-L_w)^2+(a_{rc}-a_w)^2+(b_{rc}-b_w)^2]^{1/2}=66.2$$

The ΔΔE value for the product/transparent region of the product for each reference colour ($\Delta\Delta E_p$) is then calculated using the following formula:

$$\Delta\Delta E_{p/rc}=[(L_{rc}-L_p)^2+(a_{rc}-a_p)^2+(b_{rc}-b_p)^2]^{1/2}$$

Transparency of the product for each reference colour is determined according to the formula:

$$\text{Transparency} = 100 - \frac{\Delta\Delta E_{rc} \cdot 100}{\Delta\Delta E_p}$$

The total transparency is the average value of the transparency for each reference colour, i.e.

$$TotalTransparency = 100 \cdot \frac{Transparency_{cyan} + Transparency_{magenta} + Transparency_{yellow}}{3}$$

Figure 2:
FIG. 2 illustrates the test procedure for determining colour transparency.

An example on how to carry out the above-outlined test is shown in FIG. 2.

b) Viscosity Test

The instrument used to perform the viscosity tests was a Reologica STRESSTECH ETC-3 Cell with a tool geometry as follows: cone plate 40 mm, angle 3 degrees. The temperature was set to 150° C. and the shear rate to 10 s$^{-1}$. The procedure used is as follows:

Insert the cone plate tool and set the temperature at 150° C.

Wait 15 min to reach the right temperature of the tool.

Make the zero gap by the autozero function.

Performing the sample use the autogap function, applying max. 1 N of stress.

After the sampling wait 120 seconds as equilibrium time.

Integration time 30 seconds.

Chose the value of viscosity measured at 50 sec.

c) Water Absorption Test for the Polymeric Base Material

The determination of the water absorption of the polymeric base material is conducted according to the standard test method ASTM D 570-81 with the following conditions: The measurement of water absorption for thermoplastic polymeric compositions is made on the material in form of a film sample 76.2 mm long by 25.4 mm wide by 0.2 mm thick. For all materials a 24 hours immersion in distilled water at 23° C. was chosen and the percentage of water absorbed was reported in accordance with the ASTM D 570-81 standard.

d) Water Absorption Test for the Liquid Absorbent Thermoplastic Composition

The total liquid absorption capacity of the liquid absorbent thermoplastic composition is determined as follows:

Principle:

The sample is weighed and submerged in the test solution for 10 minutes and afterwards weighted to determine the total absorption capacity.

Preparation of Saline Solution:

9 g±0.1 g NaCl is added to deionised water to give a total mass of 1000 g±0.1 g (saline solution 0.9%) and stirred until dissolved.

Apparatus and Materials:

1. Bag (100×50 mm) heat-sealable polyester mesh, folded and heat sealed on two (longer) of the three open sides so the inside edges of the seals are about 3 to 5 mm from the edge of the bag. Polyester mesh characteristic: Mass per unit area: 48 g/m$^2$, Thickness: 60 μm, Holes dimension: 18 μm, Open area: 13%, Yarn diameter: 31 μm, Number of yarn: 200/cm. Suggested supplier: Saatitech; Reference material: PES 18/13
2. Heat sealer capable of bonding polyester.
3. Analytical balance, capable of measuring a mass of 100 g to an accuracy of ±0.001 g.
4. Weighting silicon paper.
5. Timer.
6. Beaker capable of containing 1 litre of solution.
7. Spatula.
8. Tweezers.

Sample Preparation

Starting from an absorbent article the liquid absorbent thermoplastic composition can be isolated with known means in order to be tested. Typically, in an absorbent article the topsheet is removed from the backsheet and both are separated from any additional layers if present. The liquid absorbent thermoplastic composition is removed from its substrate layer, e.g. by scraping with a spatula. The liquid absorbent thermoplastic composition will be used to prepare samples as mentioned below with known means. For example, the thermoplastic composition can be melted, or dissolved with a suitable solvent. The recovered composition must be kept in a closed container to avoid dust contamination and be allowed to equilibrate to the temperature to run the test. The test conditions are 23° C.±2° C. and 50±10% relative humidity.

Procedure

1. Weigh 0.200 g±0.005 g of the liquid absorbent thermoplastic composition and record the mass (Wd).
2. Prepare a sufficient number of bags (i.e., 6) to run the required replicates.
3. Place each single test portion of 0.200 g±0.005 g of the liquid absorbent thermoplastic composition into each single bag and seal the bags opened side.

4. Prepare two blank bags (i.e. without any composition) and test alongside the bags containing the thermoplastic composition.
5. Fill the beaker with 0.9% saline solution.
6. Submerge the bags in the saline solution. Eliminate entrapped air bubbles by manipulation of the bag.
7. After 10 minutes (±10 seconds), remove the bags from saline solution and hang them freely to drain vertically till no liquid is dripping from them.
8. Weigh each single bag recording the masses of the two blanks (Wb) 1 and 2 and the masses of bags containing the absorbent composition (Ww) 1, 2, . . . n.

Calculation and Results

Calculate the average of the two wet blank bags masses after absorption $$Wb=(Wb1+Wb2)/2$$

For each sample calculate:

$$Abs(g/g)=(Ww-Wb-Wd)/Wd$$

Where:

Wd=dry test portion mass in g.
Wb=average of 2 blank bag masses (after absorption) in g.
Ww=mass of wet bag containing liquid absorbent thermoplastic composition in g.

e) Thickness Measurement

The thickness of a film of the liquid absorbent thermoplastic composition of the present invention should always be measured at the thickest possible place. The thickness is measured with a micrometer gauge having a range of 0 to 30 mm and capable of plus minus 0.5 mm tolerance. The gauge must not be spring-loaded and should have a foot moving downwards under gravity. The micrometer foot has a diameter of 40 mm and is loaded with 80 gram weight. The measurement is taken between 5 and 10 seconds after the foot has been lowed to come into contact with the absorbent article. Measurements should be taken often enough to allow statistical analysis to determine average thickness within a sigma of plus minus 0.1 mm. A detailed description of the thickness measurement can also be found in U.S. Pat. No. 5,009,653.

f) Tensile Strength Test

The test measures the mechanical resistance of a sample of material as tensile strength at break, according to the standard test method ASTM D 412-92, under the following conditions. The test is performed on samples made of the liquid absorbent thermoplastic composition of the present invention having a length of 130 mm, a width of 25.4 mm, and a thickness of 2 mm, and being continuous, obtained with any suitable method, for example by pouring the liquid absorbent thermoplastic composition in molten state at a suitable temperature, e.g. 180° C. for the compositions of Examples 2 or 3, into a metallic pan lined with release paper in a continuous layer having a thickness of 2 mm, and then after cooling cutting from this layer the samples of the desired dimensions. The test is performed on samples made of the same composition both in dry and in wet state. In order to prepare the samples in wet state a sample is placed in a container of a saline solution (e.g. 0.9% NaCl distilled water solution) maintained at a temperature of 23±1° C., and shall rest entirely immersed for ten minutes. At the end of ten minutes, the sample shall be removed from the water, all surface water wiped off with a dry cloth, and tested for wet tensile strength as provided in the standard test method.

g) Alternative Sample Preparation for All Test Herein When Starting from an Absorbent Article When starting from an article comprising the liquid absorbent thermoplastic composition, for example a disposable absorbent article with the liquid absorbent thermoplastic composition coated onto a substrate, the liquid absorbent thermoplastic composition can be isolated with known means in order to be tested. Typically, in a disposable absorbent article the topsheet is removed from the backsheet and both are separated from any additional layers if present. The liquid absorbent thermoplastic composition is removed from its substrate layer, e.g. by scraping with a spatula. The recovered liquid absorbent thermoplastic composition will be used to prepare samples as mentioned above with known means. For example, the liquid absorbent thermoplastic composition can be melted, or dissolved with a suitable solvent. Particles of superabsorbent material can be also separated from the polymeric base material, in order to isolate the polymeric base material, as it is known in the art, for example by suitably sieving or filtering from the molten state, or preferably from the solution.

EXAMPLES

The particle size of the Aqua Keep 10SH-NF particles used in all the following examples was between 20 and 30 μm, the particles were approximately spherical beads.

1.) Examples for the liquid absorbent thermoplastic composition of the present invention are:

Example 1

An example for the liquid absorbent thermoplastic composition of the present invention is the following mixture, forming a hot-melt adhesive:

| | |
|---|---|
| 18% | Estane T5410 from Noveon |
| 17% | PEG E400 from Dow Chemical |
| 1% | Irganox B 225 from Ciba Speciality Chemicals |
| 19% | CR00 (former PM17) from Savare |
| 45% | Aquakeep 10 SH-NF from Sumitomo-Seika. |

Estane T5410 is a hydrophilic polyurethane thermoplastic polymer, PEG E400 is a polyethylene glycol (plasticizer, MW about 400), Irganox B 225 an anti oxidant and CR00 is commercially available hotmelt adhesive.

Example 2

A thermoplastic polyether-amide block copolymer available from Atofina (France) under the trade name Pebax MV 3000 is compounded with polyethylene glycol PEG 400 (plasticiser, MW about 400), Sodium Dodecyl Sulphate (SDS), both available from Aldrich Co., and Irganox B 225 (anti oxidant agent) available from Ciba-Geigy. The formulation in percent by weight has the following composition, and constitutes the thermoplastic polymeric base material:

| | |
|---|---|
| 28.6% | Pebax MV 3000 |
| 68.6% | PEG 400 |
| 1.4% | SDS |
| 1.4% | Irganox B 225 |

The thermoplastic polymeric base material has a water absorption of 43%, value measured according to the Water Absorption Test described herein. The polymeric base material is formed into a film to be used in the Water Absorption Test by melt coating the thermoplastic base material at a temperature of 180° C. onto a release paper to obtain a film having the prescribed thickness of 200 μm. After cooling at room temperature the film is separated from the release paper.

A superabsorbent material in particle form, sold under the trade name Aqua Keep 10SH-NF by Sumitomo Seika Chemical (Japan), is added to the thermoplastic polymeric base material while maintained at a temperature of 180° C. and uniformly dispersed, in an amount corresponding to 42.9% by weight of the above thermoplastic polymeric base material. This example of the liquid absorbent thermoplastic composition has the following final composition by weight:

| | |
|---|---|
| 20% | Pebax MV 3000 |
| 48% | PEG 400 |
| 30% | Aqua Keep 10SH-NF |
| 1% | SDS |
| 1% | Irganox B 225 |

Example 3

A thermoplastic polyether-ester block copolymer available from Du Pont (USA) under the trade name Hytrel 8171 is compounded with polyethylene glycol PEG 400 (plasticiser, MW about 400), polyethylene glycol PEG 1500 (plasticiser, MW about 1500), both available from Aldrich Co., and Irganox B 225 (anti oxidant agent) available from Ciba-Geigy. The formulation in percent by weight has the following composition, and constitutes an alternative thermoplastic polymeric base material:

| | |
|---|---|
| 28.6% | Hytrel 8171 |
| 21.4% | PEG 400 |
| 48.6% | PEG 1500 |
| 1.4% | Irganox B 225 |

The thermoplastic polymeric base material has a water absorption of 96%, value measured according to the Water Absorption Test described herein. The thermoplastic base material is formed into a film to be used in the Water absorption Test by melt coating the thermoplastic base material at a temperature of 180° C. onto a release paper to obtain a film having the prescribed thickness of 200 μm. After cooling at room temperature the film is separated from the release paper.

A superabsorbent material in particle form sold under the trade name Aqua Keep 10SH-NF by Sumitomo Seika Chemical (Japan) is added to the thermoplastic polymeric base material while maintained at a temperature of 180° C. and uniformly dispersed, in an amount corresponding to 42.9% by weight of the thermoplastic polymeric base material. As another illustrative example of the present invention, the resulting liquid absorbent thermoplastic composition has the following final composition by weight:

| | |
|---|---|
| 20% | Hytrel 8171 |
| 15% | PEG 400 |
| 34% | PEG 1500 |
| 30% | Aqua Keep 10SH-NF |
| 1% | Irganox B 225 |

All these exemplary compositions (Examples 1 to 3) respectively have a tensile strength in wet state, which is at least 35% of the tensile strength of the composition in dry state, when evaluated according to the Tensile strength test described herein. All these exemplary compositions (Examples 1 to 3) respectively have a total absorption capacity towards saline solution (0.9%) of more than 5 grams per gram when measured according to test described herein before.

2.) Exemplary absorbent articles according to the present invention are described herein after:

Example 4

A panty liner comprises an apertured polyethylene formed film topsheet (Transparent TS3 coded X28278 available from Tredegar), a spiral layer of adhesive (D3151 available from Fuller), a Secondary Topsheet nonwoven material (carded bico Sawabond 4314 available from Sandler), an adhesive absorbent core consisting of the composition of Example 2, a plastic polyethylene film backsheet without pigment (code 14/18020, available from RKW) and panty fastening adhesive (HL1461 available from Fuller). The topsheet, the secondary topsheet, the absorbent core and the backsheet are substantially coextensive with each other and are attached to each other along the outer edge of the so-formed panty liner by heat bonding.

Example 5

A sanitary napkin comprises an apertured film topsheet (CPM RIS coded 1035025 available from Tredegar) as the uppermost layer, a 40 g/m$^2$ BICO thermalbonded carded nonwoven secondary topsheet from Sandler (coded Sawabond 4313) underneath the topsheet and a polyethylene backsheet from RKW (coded RKPA) as the lowest layer. Between the secondary topsheet and the backsheet the liquid absorbent thermoplastic composition of example 2 is applied in stripes, which are substantially parallel to the longitudinal centreline of the so-formed sanitary napkin, thus forming the absorbent core. The topsheet, the secondary topsheet, the absorbent core and the backsheet are substantially coextensive with each other and are attached to each other along the outer edge of the so-formed napkin by heat bonding. On the outer surface of the backsheet a layer of the panty fastening adhesive LA 204 from Savare was applied.

Example 6

A sanitary napkin as in Example 5, said napkin comprising in addition to the elements mentioned in Example 5 a fibrous layer underlying the storage layer, i.e., between the absorbent core and the backsheet. This fibrous layer is a spunlaced nowoven layer.

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising an absorbent core, said absorbent core comprises a liquid absorbent thermoplastic composition comprising
a water absorbent polymeric base material, and
particles of superabsorbent material;
wherein said particles of superabsorbent material have a substantially angle-lacking shape and said particles of superabsorbent material have an average particle diameter in dry state of from about 0.1 µm to about 500 µm.

2. The disposable absorbent article of claim 1, wherein said article has in at least one region a transparency value of at least 50%.

3. The disposable absorbent article of claim 1, comprising a topsheet and a backsheet, said absorbent core being positioned between said topsheet and said backsheet, wherein said topsheet, said backsheet and said absorbent core are made of substantially transparent material.

* * * * *

UNITED STATES PATENT AND TRADEMARK OFFICE
CERTIFICATE OF CORRECTION

PATENT NO. : 7,321,007 B2
APPLICATION NO. : 10/670043
DATED : January 22, 2008
INVENTOR(S) : Ivano Gagliardi et al.

It is certified that error appears in the above-identified patent and that said Letters Patent is hereby corrected as shown below:

Column 1
Line 37, delete "absoroent" and insert -- absorbent --.

Column 7
Line 54, delete "thereof" and insert -- thereof. --.

Column 8
Line 41, delete "Vectorm" and insert -- Vector$^{TM}$ --.

Column 9
Line 1, delete "Exactm." and insert -- Exact$^{TM}$. --.

Column 10
Line 23, delete "245" and insert -- 2-45 --.

Column 15
Line 20, delete "g.e." and insert -- e.g. --.

Column 17
Line 16, delete "$\Delta\Delta_w$," and insert -- $\Delta\Delta E_w$, --.

Signed and Sealed this

Seventeenth Day of June, 2008

JON W. DUDAS
*Director of the United States Patent and Trademark Office*